United States Patent
Adachi et al.

(10) Patent No.: US 6,855,850 B2
(45) Date of Patent: Feb. 15, 2005

(54) METHOD OF MANUFACTURING FLUORINE COMPOUNDS, AND A METHOD OF RECOVERING OR REGENERATING PRECURSORS OF FLUORINATING AGENTS

(75) Inventors: Kenji Adachi, Tsukuba (JP); Ginjiro Tomizawa, Tsukuba (JP); Satoshi Oishi, Tsukuba (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 10/426,726

(22) Filed: May 1, 2003

(65) Prior Publication Data

US 2003/0216603 A1 Nov. 20, 2003

(51) Int. Cl.$^7$ .......................... C07C 45/00; C07C 22/00; C07D 221/02; C07D 241/00
(52) U.S. Cl. ........................ 568/323; 568/328; 570/143; 546/112; 546/346; 544/336; 544/409
(58) Field of Search ................................. 568/323, 328; 570/143; 546/112, 346; 544/336, 409

(56) References Cited

U.S. PATENT DOCUMENTS 5,606,084 A * 2/1997 Poss et al. .................. 552/600
5,631,372 A * 5/1997 Poss et al. .................. 544/352

OTHER PUBLICATIONS

Umemoto et al. Synthesis, Properties, and Reactivity of N,N–Difluorobipyridinium and Related Salts and Their Applications as Reactive and Easy to Handle Electrophilic Fluorinating Agents . . . ☐☐Journal of Organic Chemistry, 1998, vol. 63, p 3379–3385.*

Manandhar et al., Electrophilic Fluorinating Reagent Mediated Synthesis of Fluorinated alpha–Keto Ethers, Benzil, and 6,6–Dialkoxy–2,2–bipyridines.☐☐Journal of Organic Chemistry, 2002, vol. 67 p 6415–6420.*

* cited by examiner

Primary Examiner—Johann Richter
Assistant Examiner—Sikarl A. Witherspoon
(74) Attorney, Agent, or Firm—Armstrong, Kratz, Quintos, Hanson & Brooks, LLP

(57) ABSTRACT

To provide a practical method of manufacturing fluorine compounds in a small number of steps that can carry out fluorination reaction of substrates using easily available fluorinating agents that can be inexpensively produced industrially, and recover precursors of the fluorinating agents generated accompanying the reaction quantitatively in an easy operation, and a method of recovery and regeneration of the precursors of the fluorinating agents.

N-Fluoro-quaternary-nitrogen-onium tetrafluoroborate salts represented by the general formula (1) as the fluorinating agents are used.

N-Hydro-quaternary-nitrogen-onium tetrafluoroborate salts represented by the general formula (2) generated accompanying the reaction are separated and recovered from the reaction mixture by means of depositing as crystals by the addition of solvents with a low affinity to the salts to the reaction mixture after the reaction.

General formula (1):

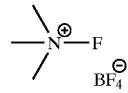

General formula (2):

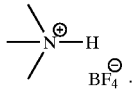

9 Claims, No Drawings

US 6,855,850 B2

METHOD OF MANUFACTURING FLUORINE COMPOUNDS, AND A METHOD OF RECOVERING OR REGENERATING PRECURSORS OF FLUORINATING AGENTS

TECHNICAL FIELD OF THE INVENTION

The present invention relates to a method of manufacturing fluorine compounds, and a method of recovering or regenerating precursors of fluorinating agents.

PRIOR ART

N,N'-Difluoro-2,2'-bipyridinium salt is known as an electrophilic fluorinating agent industrially available at low cost and used in fluorination of various organic compounds (substrates) (T. Umemoto, N. Nagayoshi, K. Adachi, and G. Tomizawa, J. Org. Chem., 1998, 63, 3379).

Besides the above, various electrophilic fluorinating agents are reported in literature, etc. (for example; T. Umemoto, S. Fukami, G. Tomizawa, K. Harasawa, K. Kawada, and K. Tornita, J. Am. Chem. Soc., 1990, 112, 8563, Ronald Eric Banks, J. Fluorine Chem., 1998, 87, 1, Andrew J. Poss and George A. Shia, Tetrahedron Lett., 1999, 40, 2673, G. Sankar Lal, Guido P. Pez, and Robert G. Syvret, Chemical Reviews, 1996, 96, 1737–1755).

In fluorination reactions using any fluorinating agents, the N—F bonds of the fluorinating agents are cleaved and nitrogen compounds that the fluorinating agents generate by losing fluorine atoms are formed accompanying formation of the objective fluorine compounds. The nitrogen compounds are useful precursors of fluorinating agents that can regenerate fluorinating agents by treatment with fluorine, etc.

However, there are only a few reports on the method of recovering and reusing nitrogen compounds that are precursors of the fluorinating agents, and even the reports lack practicability in the extreme.

For example, Japanese Patent Application Laid-Open 1993-294937 describes a method of fluorination using substituted N-fluoropyridinium sulfonates as fluorinating agents.

In the examples shown in the publication,
N-fluoro-3-chloro-5-(trifluoromethyl)-pyridinium-2-sulfonate,
N-fluoro-5-(trifluoromethyl)pyridinium-2-sulfonate, or
N-fluoro-4,6-dimethylpyridinium-2-sulfonate is used as the fluorinating agent in the fluorination of 2-oxocyclopentanecarboxylic acid ethyl-ester or its anion.

After the reactions, the pyridine compounds formed are recovered as precipitates in the following rates of recovery. Namely, the rate of recovery of 3-chloro-5-trifluoromethyl-2-pyridinesulfonic acid is 83%, the rate of recovery of 5-trifluoromethyl-2-pyridinesulfonic acid is 86% when the reaction solvent is acetonitrile and 96% when the reaction solvent is 1,2-dichloroethane, and the rate of recovery of 4,6-dimethylpyridine-2-sulfonic acid sodium salt is 85%.

Although the rates of recovery are fairly high, since the fluorinating agents described above are those with counter anions comprised of sulfonic acid groups bonded to pyridine rings, their production requires difficult-to-obtain raw materials and multi-step processes. Therefore, the method using the fluorinating agents described above has a practical problem that it is difficult to adopt industrially.

The method of recovery and reuse of precursors of fluorinating agents that seems to be most successful is the one disclosed in Japanese Patent Application Laid-Open 2002-030012. The method uses N,N'-difluoro-2,2'-bipyridinium bis(perfluoroalkanesulfonate) as the fluorinating agent, precipitates N,N'-dihydro-2,2'-bipyridinium bis (perfluoroalkanesulfonate) (abbreviated as precursor below), that is produced accompanying the fluorination reaction, and recovers it by filtration with rates of recovery that reaches 96%.

Even in the method, however, since the precursors are highly soluble in the reaction solvent, in order to raise the rate of recovery it is necessary to add a solvent having low affinity with the precursor after the reaction solvent is distilled off and the precursor is sufficiently concentrated to replace the reaction solvent solvated to the precursor with the solvent.

Further, even at the highest rate of recovery of 96%, the remaining 4% cannot be recovered and is discarded. If the discarded precursors of fluorinating agents are discharged into the natural world, they may adversely affect the environment.

OBJECT OF THE INVENTION

The present invention was accomplished in view of the above-described circumstance, with the purpose of providing a practical method of manufacturing fluorine compounds in fewer steps, capable of carrying out fluorination reaction of substrates using fluorinating agents that can be produced industrially at low cost and are easily available, and quantitatively recovering in an easy operation the precursors of fluorinating agents formed accompanying the reaction, and a method of recovering or regenerating the precursors of fluorinating agents.

CONSTITUTION OF THE INVENTION

Namely, the present invention relates to a method of manufacturing fluorine compounds that carries out fluorination reaction of substrates using an N-fluoro-quaternary-nitrogen-onium tetrafluoroborate salt as a fluorinating agent represented by the general formula (1):

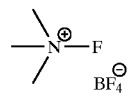

and recovers an N-hydro-quaternary-nitrogen-onium tetrafluoroborate salt represented by the general formula (2):

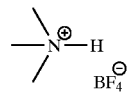

formed accompanying the reaction from the reaction mixture after the reaction, and also relates to a method of recovery or regeneration of precursors of said fluorinating agents that carries out fluorination reaction of said substrates using said N-fluoro-quaternary-nitrogen-onium tetrafluoroborate salt as said fluorinating agent and recovers said N-hydro-quaternary-nitrogen-onium tetrafluoroborate salt formed accompanying the reaction from said reaction mixture after the reaction.

According to the present invention, said N-fluoro-quaternary-nitrogen-onium tetrafluoroborate salts are said fluorinating agents that can be produced industrially at low cost and are easily available, and said N-hydro-quaternarynitrogen-onium tetrafluoroborate salts formed accompanying the fluorination reaction are compounds that can be easily separated and recovered from said reaction mixture by such methods as deposition by crystallization of the salts by the addition of solvents with a low affinity to the salts to said reaction mixture.

Said N-hydro-quaternary-nitrogen-onium tetrafluoroborate salts are nitrogen compounds having the same counter anion as said N-fluoro-quaternary-nitrogen-onium tetrafluoroborate salts, and are compounds useful as precursors of said fluorinating agents that regenerate said N-fluoro-quaternary-nitrogen-onium tetrafluoroborate salts upon treatment with, e.g., fluorine.

According to the present invention, since said N-hydro-quaternary-nitrogen-onium tetrafluoroborate salts can be recovered almost completely, it can provide an industrially and economically superior environmentally-friendly method of manufacturing fluorine compounds with very little fear of contaminating the environment with waste fluid.

PREFERRED EMBODIMENTS OF THE INVENTION

The present invention will be further specifically described below based on its embodiments.

In the present invention, it is preferable to fluorinate said recovered N-hydro-quaternary-nitrogen-onium tetrafluoroborate salts with fluorine gas, etc. to form said N-fluoro-quaternary-nitrogen-onium tetrafluoroborate salts, and to use the products as said fluorinating agents in fluorination reaction of said substrates.

In the present invention, it is preferable to crystallize, precipitate, and filtrate to recover said N-hydro-quaternary-nitrogen-onium tetrafluoroborate salts from said reaction mixtures after said fluorination reactions by addition of solvents, that are less polar than the solvents used in said fluorination reactions and have low affinity to said N-hydro-quaternary-nitrogen-onium tetrafluoroborate salts, to said reaction mixtures.

Further, regardless of the above description, when, for example, the fluorinated product formed by said fluorination reaction is volatile, it is preferable to distill the reaction solvent and the fluorinated product off said reaction mixture after said fluorination reaction, to recover said N-hydro-quaternary-nitrogen-onium tetrafluoroborate salt as a residue.

Further, the distilled solvent can be recovered and reused as it is or after purification. This applies to all the solvents distilled off in implementation of the present invention.

Further, when the fluorinated product formed by said fluorination reaction is not volatile, it is preferable to recover said N-hydro-quaternary-nitrogen-onium tetrafluoroborate salt by crystallization, precipitation, and filtration by addition of a solvent less polar than the reaction solvent used in said fluorination reaction with a lower affinity to said N-hydro-quaternary-nitrogen-onium tetrafluoroborate salt to the residue after partial or total distillation of the reaction solvent from said reaction mixture after said fluorination reaction.

In the present invention, said N-fluoro-quaternary-nitrogen-onium tetrafluoroborate salt is preferably N,N'-difluoro-2,2'-bipyridinium bis(tetrafluoroborate), 1-(chloromethyl)-4-fluoro-1,4-diazoniabicyclo[2.2.2]octane bis(tetrafluoroborate), or 1-hydroxy-4-fluoro-1,4-diazoniabicyclo[2.2.2]octane bis(tetrafluoroborate), represented by the following formulas (3) through (5).

Formula (3):

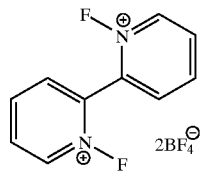

Formula (4):

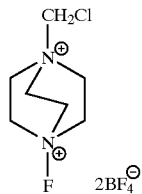

Formula (5):

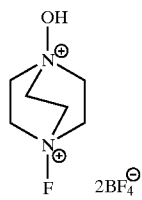

The embodiment of the present invention will be explained below in further detail along by the reaction steps.

Fluorination Reaction of Substrates

In the embodiment of the present invention, the N-fluoro-quaternary-nitrogen-onium tetrafluoroborate salts synthesizable by the method known in the literature shown above are preferably used without isolation to carry out the fluorination reaction in a single step by mixing with substrates.

If necessary, however, N-fluoro-quaternary-nitrogen-onium tetrafluoroborate salts can be isolated once, and the isolated N-fluoro-quaternary-nitrogen-onium tetrafluoroborate salts can be used for the fluorination reaction.

The substrates can be added to the reaction mixture of N-fluoro-quaternary-nitrogen-onium tetrafluoroborate salts, or inversely N-fluoro-quaternary-nitrogen-onium tetrafluoroborate salts can be added to the reaction mixture of the substrates.

Further, the reaction solvents used in the synthesis of N-fluoro-quaternary-nitrogen-onium tetrafluoroborate salts can be used as they are as the solvent for fluorination of substrates, or a plurality of other solvents can also be added. Kinds of reaction solvents may also be changed if necessary.

Reaction temperature may be in the range of −30° C. to 150° C., and preferably −10° C. to 100° C.

As the objective substrates of fluorination of the present invention, those already reported (T. Umemoto, M. Nagayoshi, K. Adachi, and G. Tomizawa, J. Org. Chem., 1998, 63, 3379; G. Sankar Lal, Guido P. Pez, and Robert G. Syvret, Chemical Reviews, 1996, 96, 1737–1755) may be cited, while any substrates susceptible to electrophilic fluorination may be used without limitation.

Recovery of Precursors of Fluorinating Agents

In order to recover N-hydro-quaternary-nitrogen-onium tetrafluoroborate salts formed accompanying fluorination reactions, it is preferable to crystallize, precipitate, and filter the salts by addition of a solvent such as one less polar than the reaction solvent used in the fluorination reaction, with a lower affinity to the salts, and low solubility of N-hydro-quaternary-nitrogen-onium tetrafluoroborate salts, to the reaction mixture after the fluorination reaction.

Further, when the fluorinated product formed by the fluorination reaction is volatile, all the reaction solvent and the fluorinated product maybe distilled off the reaction mixture after fluorination reaction, and N-hydro-quaternary-nitrogen-onium tetrafluoroborate salts may be separated from the residue or the residue may be used as it is for the next reaction.

Further, when the fluorinated product formed by the fluorination reaction is not volatile, it is preferable to recover N-hydro-quaternary-nitrogen-onium tetrafluoroborate salt by crystallization, precipitation, and filtration of the salt by addition of a solvent less polar than the reaction solvent used in the fluorination reaction, with a lower affinity to N-hydro-quaternary-nitrogen-onium tetrafluoroborate salt and in which N-hydro-quaternary-nitrogen-onium tetrafluoroborate salt is less soluble, to the residue after part or all of the reaction solvent is distilled off the reaction mixture after the fluorination reaction.

As a solvent in which N-hydro-quaternary-nitrogen-onium tetrafluoroborate salt has low solubility, ether-type solvents such as diethyl ether, tetrahydrofuran, 1,2-dimethoxyethane, 1,2-diethoxyethane, triglyme, tetraglyme and dioxane, ester-type solvents such as ethyl acetate, methyl acetate, ethyl formate, methyl propionate, and ethyl propionate, aromatic solvents such as benzene, toluene, chlorobenzene, fluorobenzene, and ethylbenzene, and aliphatic hydrocarbon solvents such as hexane, pentane, and petroleum ether are preferable, which may be used alone or as a mixture of two or more solvents selected from them.

Although recovered N-hydro-quaternary-nitrogen-onium tetrafluoroborate salt may contain a little of compounds in which unreacted N—F bonds are left when the fluorinating agent is used slightly in excess relatively to the substrate, regeneration of the fluorinating agent with fluorine gas can be carried out as it is without any problem.

Isolated N-hydro-quaternary-nitrogen-onium tetrafluoroborate salts may be reused for preparation of N-fluoro-quaternary-nitrogen-onium tetrafluoroborate salts as they are, while they can be dried or re-crystallized if necessary.

Regeneration of Fluorinating Agent

N-hydro-quaternary-nitrogen-onium tetrafluoroborate salts recovered as described above can be turned back to N-fluoro-quaternary-nitrogen-onium tetrafluoroborate salts in one step by fluorinating with fluorine gas (for example, T. Umemoto, M. Nagayoshi, K. Adachi, and G. Tomizawa, J. Org. Chem., 1998, 63, 3379; Lal, G. S., J. Org. Chem., 1993, 58, 2791)

As the solvent used in the fluorination of N-hydro-quaternary-nitrogen-onium tetrafluoroborate salts, halogenated aliphatic hydrocarbon solvents such as dichloromethane, dichloroethane, chloroform, 1,1,2-trichlorotrifluoroethane, and 1,1,1-trichlorotrifluoroethane, nitrile compounds such as acetonitrile and propionitrile, formic acid, acetic acid, trifluoroacetic acid, etc. are preferable, and mixtures of two or more of these solvents can also be used.

As described above, the solvents may be used as they are as the reaction solvents for fluorinating substrates.

Although said fluorine gas may be introduced as a pure gas, mixed gases diluted with gases inert to fluorination reaction (such as nitrogen, argon, helium, etc.) containing 1% to 50%, preferably 5 to 30%, by volume of fluorine are preferably used from the viewpoint of safety.

Although fluorine gas is preferably used in an amount not less than equivalent to N—H of the N-hydro-quaternary-nitrogen-onium tetrafluoroborate salts, the most adequate amount of fluorine may be selected depending on conditions such as the reaction temperature, reaction solvent, and method of introducing the fluorine gas.

The reaction temperature may be in the range of −30° C. to 40° C. and preferably in the range of −10° C. to 25° C.

Recovery of Fluorinated Products

When the fluorinated products are volatile, they are desirably isolated by distillation directly after the reaction. When they are not volatile, it is desirable that they are dissolved in the reaction solvent or the cleaning solvent, and after distilling off the solvent they may be purified by suitable methods (such as re-crystallization, column chromatography, etc.). The fluorinated products can be used as intermediates for pharmaceutical synthesis, intermediates for agrochemical synthesis, intermediates for liquid crystal synthesis, etc.

As described above, with fluorinating agents having tetrafluoroborate $BF_4^-$ as a counter anion, that can be synthesized by the methods known by the literature shown earlier, N-hydro-quaternary-nitrogen-onium tetrafluoroborate salts formed accompanying the fluorination reaction are easily recovered and regenerated. Further, regenerated N-fluoro-quaternary-nitrogen-onium tetrafluoroborate salts may also be used continuously in fluorination reactions without isolation.

The present invention is characterized in that it realizes an almost 100% recovery rate concerning recovery of 2,2'-bipyridinium salt disclosed in the prior application, Japanese Patent Publication Laid-Open 2002-030012, surpassing the prior application by changing the counter anion from perfluoroalkane sulfonate to tetrafluoroborate.

The reason why a 100% or nearly 100% recovery rate could be realized is that the solubilities of quaternary-nitrogen-onium salts having tetrafluoroborate as their counter anion to non-polar or less-polar organic solvents were noticed to be far smaller than those of the salts having perfluoroalkane sulfonate as their counter anion.

Further, the present recovery system is a method applicable to N-fluoro-type fluorinating agents in general having tetrafluoroborate salts as their counter anions, for example; 1-(chloromethyl)-4-fluoro-1,4-diazoniabicyclo[2.2.2]octane bis(tetrafluoroborate) and 1-hydroxy-4-fluoro-1,4-diazoniabicyclo[2.2.2]octane bis(tetrafluoroborate).

The two salts mentioned above have two tetrafluoroborates in a formula, so that by discarding the salt, eight times as much fluorine atoms as the salt is discharged. Therefore, adoption of a re-utilization recycling system based on the present invention can considerably reduce the load imposed upon the environment.

The present recovery system can recover the fluorinated products in a small number of steps, and thus facilitates recovery.

EXAMPLES

Although the present invention is explained below in further detail using examples, they shall not limit the present invention at all.

Example 1

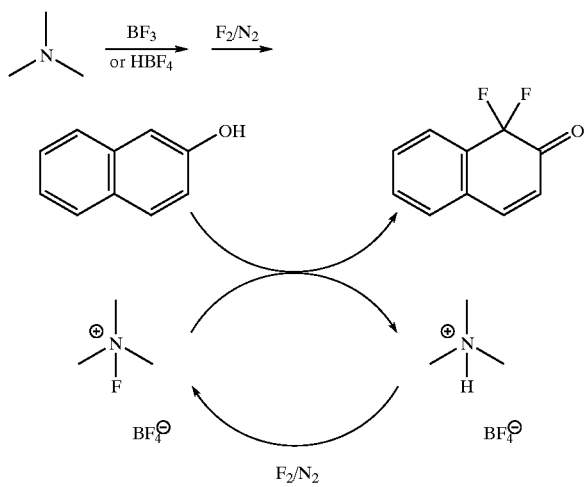

The chemical formula shown above indicates reaction flows constituting the whole process.

The precursor of a fluorinating agent, 2,2'-bipyridinium bis(tetrafluoroborate), 4.973 g (15.0 mmol), was added to 60 mL of a reaction solvent, acetonitrile, and mixed.

Next, the mixture was chilled to 0° C., and 30.3 mmol of fluorine gas diluted with nitrogen gas to 15.55% by volume was introduced at a rate of 100 mL/min to act on 2,2'-bipyridinium bis(tetrafluoroborate), to synthesize N,N'-difluoro-2,2'-bipyridinium bis(tetrafluoroborate). Then, the air in the reaction system was sufficiently replaced with nitrogen gas, 2.056 g (14.26 mmol) of 2-naphthol was added at 0° C., and the mixture was agitated for 10 minutes at the same temperature, for 18.5 hours at room temperature, and for a further 24 hours at 50° C.

After bringing it back to room temperature, 1.027 g (10.69 mmol) of an internal standard, fluorobenzene, was added, part of the reaction solution was taken, the sample was diluted with deuterated acetonitrile, and $^{19}$F-NMR was measured. As a result, an 82% yield of 1,1-difluoro-2-naphthalenone was confirmed.

The reaction mixture was concentrated by distilling off the solvent under reduced pressure, 40 mL of diisopropyl ether was added to the concentrated residue, the deposited crystals were filtered, dried under reduced pressure after rinsing with diisopropyl ether, and 4.973 g of 2,2'-bipyridinium bis (tetrafluoroborate) was recovered at a rate of 100%. The rate of recovery of 100% means a quantitative recovery. The fluorinated product, 1,1-difluoro-2-naphthalenone, is contained in the filtrate from which it can be separately recovered.

Example 2

The precursor of a fluorinating agent, 1-(chloromethyl)-4-hydro-1,4-diazoniabicyclo[2.2.2]octane bis(tetrafluoroborate), 6.725 g (20.0 mmol), was added to 40 mL of a reaction solvent, acetonitrile, and mixed.

Next, the mixture was chilled to 0° C., and 20.2 mmol of fluorine gas diluted with nitrogen gas to 15.55% by volume was introduced at a rate of 100 mL/min. Then, the air in the reaction system was sufficiently replaced with nitrogen gas, 1.423 g (9.87 mmol) of 2-naphthol was added at 0° C., and the mixture was agitated for 10 minutes at the same temperature, for 17.5 hours at room temperature, and for a further 7.5 hours at 50° C.

After bringing it back to room temperature, 1.042 g (10.84 mmol) of an internal standard, fluorobenzene, was added, part of the reaction solution was taken, the sample was diluted with deuterated acetonitrile, and $^{19}$F-NMR was measured. As a result, a 96% yield of 1,1-difluoro-2-naphthalenone was confirmed.

The reaction solution was concentrated by distilling off the solvent under reduced pressure, 40 mL of diisopropyl ether was added to the concentrated residue, the deposited crystals were filtered, dried under reduced pressure after rinsing with diisopropyl ether, and 6.655 g (19.79 mmol) of 1-(chloromethyl)-4-hydro-1,4-diazoniabicyclo[2.2.2]octane bis(tetrafluoroborate) was recovered. The rate of recovery was 99%. The fluorinated product, 1,1difluoro-2-naphthalenone, is contained in the filtrate from which it can be separately recovered.

Further, said 1,1-difluoro-2-naphthalenone is a molecule having fluorine atoms in itself, and derivatives with further substituents introduced in the naphthalene ring are useful as intermediates for the syntheses of pharmaceuticals and agrochemicals.

FUNCTION AND EFFECT OF THE INVENTION

According to the present invention, N-fluoro-quaternary-nitrogen-onium tetrafluoroborate salts used for the fluorination of substrates are fluorinating agents that can be industrially manufactured at low cost and are easily available, and N-hydro-quaternary-nitrogen-onium tetrafluoroborate salts formed accompanying the fluorination reaction can be easily separated from the reaction mixture and recovered, for example, by adding a solvent with a low affinity to the salts to the mixture after the reaction to crystallize and precipitate the salts.

N-hydro-quaternary-nitrogen-onium tetrafluoroborate salts are nitrogen compounds having the same counter anion as N-fluoro-quaternary-nitrogen-onium tetrafluoroborate salts, and are useful compounds as precursors of fluorinating agents that regenerate N-fluoro-quaternary-nitrogen-onium tetrafluoroborate salts on treatment, for example, with fluorine.

According to the present invention, since said N-hydro-quaternary-nitrogen-onium tetrafluoroborate salts can be recovered at almost all amount, an industrially and economically superior environmentally-friendly method of manufacture of fluorinated compounds that poses little concern for contaminating the environment with waste fluid can be provided.

What is claimed is:
1. A method of manufacturing fluorine compounds wherein the electrophilic fluorination of organic compounds is carried out using an N-fluoro-quaternary-nitrogen-onium tetrafluoroborate salt represented by the general formula (1):

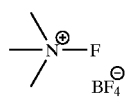

as the fluorinating agent, and the N-hydro-quaternary-nitrogen-onium tetrafluoroborate salt represented by the general formula (2):

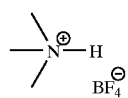

formed accompanying the reaction is recovered from the reaction mixture after the reaction; and wherein the recovered said N-hydro-quaternary-nitrogen-onium tetrafluoroborate salt is fluorinated to form the N-fluoro-quaternary-nitrogen-onium tetrafluoroborate salt, and the product is used for electrophilic fluorination of organic compounds as the fluorinating agent.

2. A method of manufacturing fluorine Compounds described in claim 1 wherein said N-hydro-quaternary-nitrogen-onium tetrafluoroborate salt is fluorinated with fluorine gas.

3. A method of manufacturing fluorine compounds described in claim 1 wherein a solvent is added to said reaction mixture after the fluorination reaction to crystallize and precipitate said N-hydro-quaternary-nitrogen-onium tetrafluoroborate salt, and to recover the same.

4. A method of manufacturing fluorine compounds described in claim 1 wherein a solvent is added to the residue after partial or total distillation of the reaction solvent from said reaction mixture after said fluorination reaction to crystallize and precipitate said N-hydro-quaternary-nitrogen-onium tetrafluoroborate salt and to recover the same.

5. A method of manufacturing fluorine compounds described in claim 3 wherein said solvent for said crystallization is a solvent less polar than the solvent used in the fluorination reaction.

6. A method of manufacturing fluorine compounds described in claim 1 wherein the reaction solvent and volatile products are distilled from said reaction mixture after said fluorination reaction to recover said N-hydro-quaternary-nitrogen-onium tetrafluoroborate salt as a residue.

7. A method of manufacturing fluorine compounds described in claim 1 wherein said N-fluoro-quaternary-nitrogen-onium tetrafluoroborate salt is N,N'-difluoro-2,2'-bipyridinium bis (tetrafluoroborate) represented by the following formula (3);

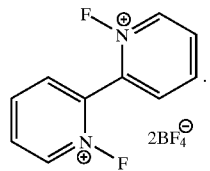

8. A method of manufacturing fluorine compounds described in claim 1 wherein said N-fluoro-quaternary-nitrogen-onium tetrafluoroborate salt is 1-(chloromethyl)-4fluoro-1,4-diazoniabicyclo[2.2.2]octane bis (tetrafluoroborate) represented by the following formula (4):

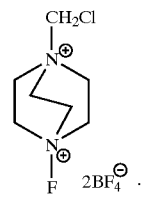

9. A method of manufacturing fluorine compounds described in claim 1 wherein said N-fluoro-quaternary-nitrogen-onium tetrafluoroborate salt is 1-hydroxy-4-fluoro-1,4-diazoniabicyclo[2.2.2]octane bis (tetrafluoroborate) represented by the following formula (5):

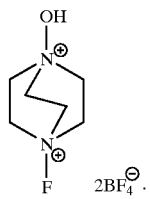

* * * * *

UNITED STATES PATENT AND TRADEMARK OFFICE
CERTIFICATE OF CORRECTION

PATENT NO. : 6,855,850 B2
DATED : February 15, 2005
INVENTOR(S) : Adachi et al.

It is certified that error appears in the above-identified patent and that said Letters Patent is hereby corrected as shown below:

<u>Title page,</u>
Insert Item -- [30]    Foreign Application Priority Data
          May 2, 2002   (JP) .....................130582/2002 --

Signed and Sealed this

Thirty-first Day of May, 2005

JON W. DUDAS
*Director of the United States Patent and Trademark Office*